US009011823B2

(12) United States Patent
Vogel et al.

(10) Patent No.: US 9,011,823 B2
(45) Date of Patent: Apr. 21, 2015

(54) ENHANCED ANTI-CARIOUS DENTIFRICES, RINSES, LOZENGES, CANDIES AND CHEWING GUMS AND METHODS OF USING SAME

(75) Inventors: Gerald L. Vogel, Germantown, MD (US); Laurence C. Chow, Potomac, MD (US); Shozo Takagi, Gaithersburg, MD (US)

(73) Assignee: ADA Foundation, Chicago, IL (US)

( * ) Notice: Subject to any disclaimer, the term of this patent is extended or adjusted under 35 U.S.C. 154(b) by 2684 days.

(21) Appl. No.: 11/048,445

(22) Filed: Feb. 1, 2005

(65) Prior Publication Data

US 2006/0171904 A1     Aug. 3, 2006

(51) Int. Cl.
*A61Q 11/00* (2006.01)
*A61K 8/21* (2006.01)
*A61K 33/04* (2006.01)
*A61K 9/68* (2006.01)
*A61K 8/30* (2006.01)

(52) U.S. Cl.
CPC ... *A61K 8/21* (2013.01); *A61K 8/30* (2013.01); *A61Q 11/00* (2013.01)

(58) Field of Classification Search
USPC ........ 424/49, 48, 52, 401, 682; 433/215, 216, 433/217.1
See application file for complete search history.

(56) References Cited

U.S. PATENT DOCUMENTS

| | | | |
|---|---|---|---|
| 4,083,955 A * | 4/1978 | Grabenstetter et al. | 424/49 |
| 4,397,837 A | 8/1983 | Raaf et al. | |
| 4,606,912 A | 8/1986 | Rudy | |
| 5,045,305 A * | 9/1991 | Clarkson et al. | 424/52 |
| 5,145,668 A | 9/1992 | Chow | |
| 5,427,768 A | 6/1995 | Tung | |
| 5,437,857 A | 8/1995 | Tung | |
| 5,476,647 A | 12/1995 | Chow | |
| 5,891,448 A * | 4/1999 | Chow et al. | 424/400 |
| 6,159,448 A | 12/2000 | Winston | |
| 6,159,449 A | 12/2000 | Winston | |
| 6,387,352 B1 | 5/2002 | Johansen | |

OTHER PUBLICATIONS

J.C. Blake-Haskins, J.R. Mellberg and C. Snyder, "*Effect of Calcium in Model Plaque on the Anticaries Activity of Fluoride in vitro*", Journal of Dental Research, 1992; vol. 71, pp. 1482-1486.
L.C. Chow, S. Takagi, C.M. Carey and B.A. Sieck, "*Remineralization Effects of a Two-Solution Fluoride Mouthrinse: An in situ Study*", Journal of Dental Research, 2000, vol. 79, No. 4, pp. 991-995.
J. Christoffersen, M.R. Christoffersen, W. Kibalczyc and W.G. Perdok, "*Kinetics of Dissolution and Growth of Calcium Fluoride and Effects of Phosphate*", ACTA Odontol Scand 1988, vol. 46, pp. 325-336.
J.D.B. Featherstone, "*The Science and Practice of Caries Prevention*", J. Am. Dent. Assoc. 2000, vol. 131, pp. 887-899.
O. Fejerskov, A. Thylstrup and M.J. Larsen, "*Rational Use of Fluorides in Caries Prevention*", ACTA Odontol. Scand. 39: pp. 241-249 (1981).
H.W. Kaufman, M.S. Wolff, A.E. Winston and C.W. Triol, "*Clinical Evaluation of the Effect of a Remineralizing Toothpast on Dentinal Sensitivity*", J. Clin. Dent. 1999, vol. 10, pp. 50-54.
H.C. Margolis and E.C. Moreno, "*Physicochemical Perspectives on the Cariostatic Mechanisms of Systemic and Topical Fluorides*", Journal of Dental Research, 1990, vol. 69 Special Issue, pp. 606-613.
B. Ogaard, G. Rolla, K. Helgeland, "*Uptake and Retention of Alkali-Soluble and Alkali-Insoluble Fluoride in Sound Enamel in vivo After Mouthrinses with 0.05% or 0.2% NaF*", Caries Res. 17, pp. 520-524 (1983).
G. Rolla and E. Saxegaard, "*Critical Evaluation of the Composition and Use of Topical Fluorides, with Emphasis on the Role of Calcium Fluoride in Caries Inhibition*", J. Dent Res 69 (Spec. Iss.): pp. 780-785, Feb. 1990.
R.K. Rose, R.P. Shellis and A.R. Lee, "*The Role of Cation Bridging in Microbial Fluoride Binding*", Caries Research 1996, vol. 30, pp. 458-464.
K.W. Stephen, "*Discussion of Session V: Rational Use of Fluorides in Prevention and Therapy*", J. Dent. Res. Feb. 1990, vol. 69 Special Issue, pp. 820-823.
J.M. ten Cate, P.P.E. Duijsters, "*Influence of Fluoride in Solution on Tooth Demineralization*", Caries Research 1983, vol. 17, pp. 193-199.
G.L. Vogel, Y. Mao, C.M. Carey, L.C. Chow and S. Takagi, "*In vivo Fluoride Concentrations Measured for Two Hours After a NaF or a Novel Two-Solution Rinse*", Journal of Dental Research, 1992, vol. 71, pp. 448-452.
D.J. White, D.G.A. Nelson, R.V. Faller, "*Mode of Action of Fluoride: Application of New Techniques and Test Methods to the Examination of the Mechanism of Action of Topical Fluoride*", Adv. Dent. Res. 1994, vol. 8, pp. 166-174.
G.M. Whitford, M.A.R. Buzalaf and M.F.B. Bijella, "*1777 Plaque [F] After Using a NaF or Placeobo Dentifice in a Non-Fluoridated Community*", 2002 J Dent Res 81 (Spec. Iss.): 233 (Abstract 1777) http://iadr.confex.com/iadr/2002SanDiego/techprogram/abstract_17774.htm.
G.M. Whitford, M.A.R. Buzalaf, M.F.B Bijella and J.L. Waller, "Plaque Fluoride Concentrations in a Community without Water Fluoridation: Effects of Calcium and Use of a Fluoride or Placebo Dentrifice", Caries Res 2005;39:100-107.
Borovkii and Agafonov, 1994 "Stomotologiia" 1-5.
Ye. V. Borovskiy and Yu. A. Agafanov, "Remineralizing Solution and Sodium Fluoride Application Sequence Recommended for the Prevention and Treatment of Dental Caries, as Well as Treatment During the White Spot Stage", Restorative Section, Stomatologiya [Densitry], vol. 2, No. 1, pp. 5-6, Jun. 18, 1993 (and translation).
Ye. V. Borovskiy and Yu. A. Agafonov, "Effect of Mineralizing Solutions on Enamel Condition and Tooth Damage by Caries" Pediatric Dentistry 1993 (translated title and summary).

* cited by examiner

*Primary Examiner* — Lezah Roberts
(74) *Attorney, Agent, or Firm* — Banner & Witcoff, Ltd.

(57) ABSTRACT

Mouth rinses, dentifrices, lozenges, confections, chewing gums, and similar delivery vehicles containing non-toxic soluble calcium are used prior to administration of a fluoride-containing composition to increase the effectiveness of the fluoride therapy. An effective amount of calcium is released into the oral cavity and allowed to penetrate into the oral tissue. Calcium-bound fluoride deposits form in the oral tissue upon subsequent administration of the fluoride-containing composition to provide increased salivary, plaque and oral tissue fluoride concentrations.

8 Claims, 3 Drawing Sheets

ENHANCED ANTI-CARIOUS DENTIFRICES, RINSES, LOZENGES, CANDIES AND CHEWING GUMS AND METHODS OF USING SAME

This invention was made during research activities that were supported in part by Grants DE05354 and DE10840 from the NIDR to the ADAF and by a grant from the American Dental Association Foundation. It was carried out at the National Institute of Standards and Technology.

BACKGROUND OF THE INVENTION

1. Field of the Invention

The various embodiments of the present invention relate to the use of non-toxic soluble calcium compositions prior to administration of any fluoride-containing composition to enhance the anticaries effect of the fluoride compositions. More particularly, calcium compositions in any suitable form including mouth rinse, dentifrice, lozenge, confection, chewing gum and the like are administered prior to use of a fluoride-containing composition to enhance the formation of calcium-bound fluoride in plaque, on teeth and in oral tissue. The fluoride-containing compositions may be any conventional fluoride-containing products such as a fluoride rinse or a dentifrice.

2. Summary of the Related Art

Fluoride is believed to be beneficial in reducing the prevalence of dental caries. It has been demonstrated that even a small increase in the fluid concentration of fluoride in the oral cavity may have a significant effect on these processes (Featherstone, 2000, *J Am. Dent. Assoc.* 131:887-99). Studies have assessed whether the formation of bioavailable fluoride reservoirs may maintain the concentration of fluoride in plaque fluid and saliva after application of a conventional fluoride-containing rinse or dentifrice (White et al., 1994, *Adv. Dent. Res.* 8:166-74; Vogel et al., 1992, *J Dent. Res.* 71:448-52; Margolis and Moreno, 1990, *J Dent. Res.* 69 (Spec. Issue): 606-13; ten Cate and Duijsters, 1983, *Caries Res.* 17:193-99).

Among the most important "labile" oral fluoride reservoirs is calcium fluoride, $CaF_2$, or phosphate contaminated "calcium fluoride-like" deposits. Recent studies by Rose et al. (1996, *Caries Res.* 30-458-64) have suggested that much of the "labile" fluoride in plaque is bound to bacteria via calcium bridges. Regardless of the particular form, calcium appears to have a significant role in the formation of calcium-fluoride ("Ca—F") deposits. Unfortunately, Ca—F deposition in the mouth is limited by the low concentration of unbound, or bioavailable, oral calcium. Furthermore, if a high level of calcium is administered simultaneously with fluoride, very rapid $CaF_2$ formation occurs in the mouth with limited penetration into oral tissue.

Several approaches have been proposed to overcome these problems. One approach has been a two-part fluoride-releasing system in which fluoride first is released by the controlled hydrolysis of sodium hexafluorosilicate and subsequently reacts with calcium to induce a controlled "in depth" deposition of calcium-bound fluoride. Although studies have shown an increase in oral fluoride in saliva and plaque (Vogel et al., 1992, *J Dent. Res.* 71:448-52) and a reduction in the in vivo growth of caries lesions (Chow et al., 2000, *J Dent. Res.* 79:991-95), this approach has a number of limitations. First, this approach requires the formulation of commercially acceptable dentifrices and rinses compatible with a particular and unique chemistry. Second, this approach uses a fluoride source ($Na_2SiF_6$) that has not yet been approved by the Food and Drug Administration.

Other approaches to increasing fluoride deposition utilize two components: either (1) a dual compartment delivery device in which both components are simultaneously delivered (Kaufman et al., 1999, *J Clin. Dent.* 10:50-54; U.S. Pat. No. 6,387,352 to Johansen; U.S. Pat. Nos. 6,159,448 and 6,159,449 to Winston; U.S. Pat. Nos. 5,427,768 and 5,437, 857 to Tung; U.S. Pat. Nos. 5,145,668 and 5,476,647 to Chow) or (2) procedures in which the two components are sequentially applied (Borovkii and Agafonov, 1994, *Stomatologiia* 1-5; U.S. Pat. No. 4,397,837 to Raaf; U.S. Pat. No. 4,083,955 to Grabenstetter). In one example of the sequential procedure, phosphate and fluoride are used as one component and calcium is used as the other component in order to increase the formation of caries-resistant fluoridated tooth mineral ($Ca_{10}(PO4)_6F_2$). Use of phosphate, however, leads to an undesirable formation of insoluble fluorapatite in plaque and in soft tissue, rather than the desirable formation of bioavailable Ca—F deposits in these substrates.

Prior attempts to administer calcium before a fluoride product that did not include phosphate have shown little or no beneficial effects on the efficacy of the fluoride product. Blake-Haskins et al., (*J Dent. Res.* 1992; 71:1482-1486). Found that by simulating a 4.5 mMol/L calcium pre-rinse with a fluoride dentifrice in an in vitro experimental caries model, a lesion was reduced in size only 14% as compared to the use of a fluoride dentifrice alone. Similarly, Whitford et al. 2005 (*Caries Res.* 39: in press) found that a 20 mmol/L $CaCl_2$ pre-rinse used immediately before brushing with a F dentifrice had no effect on human whole plaque F concentrations when samples were collected 1 h and 12 h after brushing).

In contrast to studies using low concentrations of calcium, U.S. Pat. No. 4,606,912 to Rudy and U.S. Pat. Nos. 5,476,647 and 5,891,448 to Chow and Takagi disclose administration of relatively high levels of calcium in a phosphate-free system. These patents disclose a calcium complexing agent that is used to control Ca—F formation. These systems, however, require mixing of the calcium and fluoride components before use.

U.S. Pat. No. 6,159,449 to Winston and Usen discloses another system for increasing salivary fluoride concentration. In this system, calcium and fluoride solids are dispersed in a non-aqueous, water-miscible vehicle. Calcium and fluoride ions are simultaneously released when the product contacts saliva or other aqueous solution.

BRIEF SUMMARY OF THE INVENTION

It has been discovered that much higher levels of calcium than heretofore studied will produce an efficient deposition of oral Ca—F in the oral tissue and provide an effective level of fluoride in the oral environment. Advantageously, calcium-containing compounds are administered prior to administration of fluoride-containing compounds. The calcium can be delivered in the form of a calcium pre-rinse used prior to a fluoride product. Other delivery vehicles include, but are not limited to, lozenges or chewing gum specifically formulated to produce high levels of calcium immediately before the release of fluoride. These delivery vehicles also may include a fluoride component that releases fluoride subsequent to the release of calcium from the delivery vehicle.

Generally, the various embodiments of the present invention provide calcium-containing compounds, including but not limited to, mouth rinses, dentifrices, lozenges, confections, chewing gums and similar products, or as additives to such delivery vehicles. The compounds include soluble calcium in an amount effective for enhancing the formation of calcium-bound fluoride in plaque, on teeth and/or in oral tissue upon subsequent administration of a fluoride-containing compound. Preferably, the calcium-containing compound includes a calcium salt of a non-toxic acid having a solubility of about 0.5 grams per liter or more. More preferably, the calcium salt is a salt of an acid selected from the group consisting of gluconic acid, lactic acid, fumaric acid, glycerophosphoric acid, hydrochloric acid, citric acid, acetic acid, propionic acid, sulfuric acid, nitric acid and combinations thereof.

In one embodiment, the compound is in the form of a dentifrice and the concentration of soluble calcium is between about 0.002 to about 0.5 grams of soluble calcium per gram of dentifrice. In another embodiment, the compound is in the form of a rinse and the concentration of soluble calcium is between about 30 to about 400 millimoles per liter (mMol/L) of rinse. In yet another embodiment, the compound is in the form of a lozenge or gum and the concentration of soluble calcium is between about 0.0001 to about 0.01 moles. Preferably, the fluoride-containing composition includes no more than about 40 ppm total phosphate.

In another aspect, the various embodiments of the present invention provide compositions for enhancement of anticaries activity of fluoride administered into an oral cavity. In preferred embodiments, the compositions include a calcium-containing compound comprising calcium in an amount effective for providing a soluble calcium concentration in the oral cavity of at least about 30 mMol/L and a fluoride-containing compound separated from the calcium-containing compound. The compositions provide for the sequential release of (i) calcium from the calcium-containing compound and then (ii) fluoride from the fluoride-containing compound, with the release of fluoride occurring only after released calcium has passed at least in part into oral tissue to promote reaction of calcium and fluoride in plaque, on teeth and/or in oral tissue. Preferably, the concentration of soluble calcium is between about 30 and about 400 mMol/L, more preferably between about 40 and about 300 mMol/L, even more preferably between about 50 and about 300 mMol/L.

The various embodiments of the invention also provide methods of enhancing the cariostatic effect of fluoride on teeth. Methods are provided where (a) a calcium-containing compound is delivered into an oral cavity, with the calcium-containing compound releasing soluble calcium into the oral cavity, (b) an amount of the soluble calcium is allowed to pass into the oral tissue, and (c) a fluoride-containing compound is subsequently delivered into the oral cavity. In a preferred embodiment, the soluble calcium reacts with the fluoride-containing compound to form large amounts of calcium-fluoride deposits in plaque, on teeth and in oral tissue. Preferably, the concentration of soluble calcium is at least about 30 mMol/L. The fluoride-containing compound is delivered preferably as soon as practicable after the calcium compound, however in some embodiments it may be found desirable to delay the administration of fluoride for a time sufficient to allow an exchange of saliva in the mouth upon delivering the calcium-containing compound.

DETAILED DESCRIPTION OF THE PREFERRED EMBODIMENTS

Figure 1:
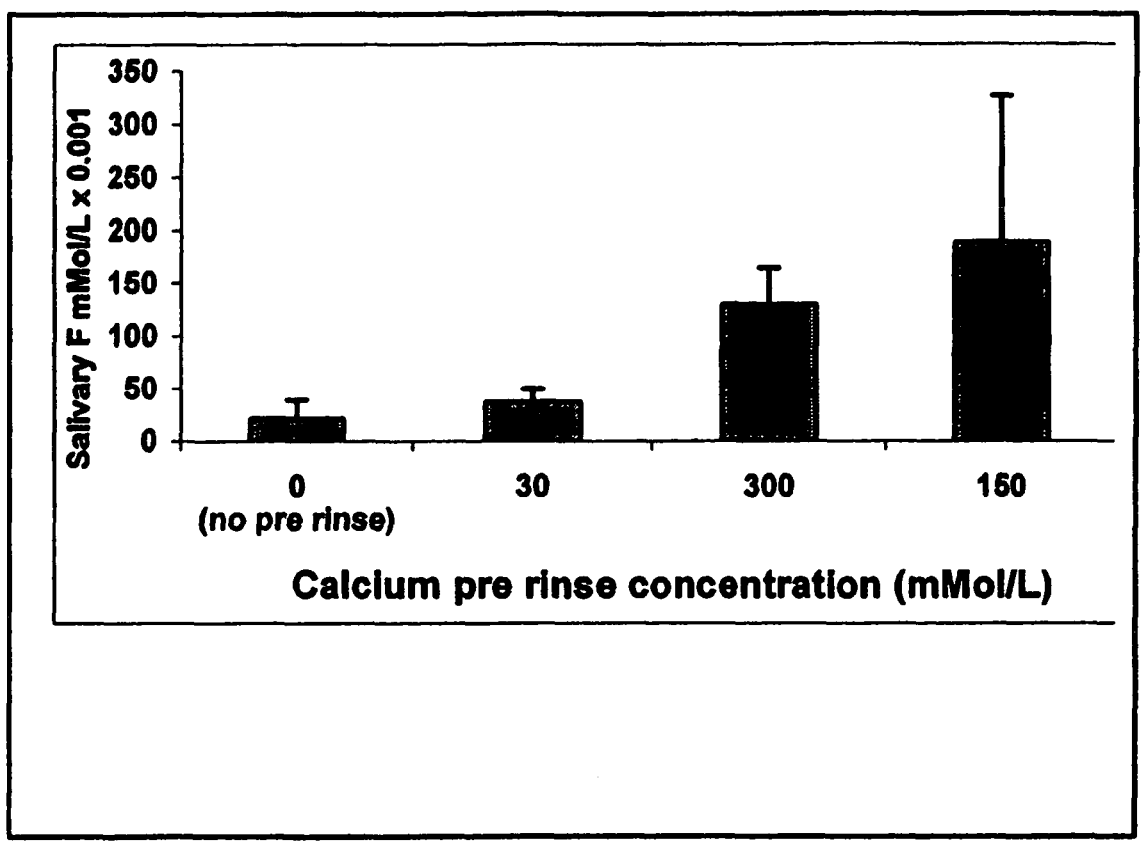
FIG. 1 is a graph showing the recorded concentrations of salivary fluoride from a group of 5 volunteers resulting from use of various calcium pre-rinses having differing concentrations of calcium.

Remineralization of tooth enamel has been carried out experimentally both in vivo and in vitro. Various fluoride therapies are known to be beneficial to de- and remineralization processes. Such fluoride therapies may include administration of a fluoride-containing product, such as a mouth rinse, dentifrice, lozenge, chewing gum or similar product. The compositions as provided herein are useful vehicles for delivering soluble calcium to oral tissue for enhancing the effectiveness, including increasing the anticaries activity, of such fluoride therapies. An advantage of these delivery vehicles is that soluble calcium and compounds that release soluble calcium ions into the oral cavity are provided as simple mixtures and delivery to oral tissue is effectively achieved by simply having a human use the delivery vehicles described herein (e.g., by administering or ingesting the compositions).

Non-toxic soluble calcium compounds may be orally administered before the administration of a fluoride-containing product. Preferably, the calcium compound is administered just prior to the administration of the fluoride-containing product. More preferably, administration of the fluoride-containing compound is delayed only for a time sufficient to allow most or all of the calcium to migrate from the oral cavity and penetrate into the oral tissue. The release of a relatively high concentration of calcium ions followed by the subsequent administration of fluoride greatly enhances the formation of calcium-bound fluoride in plaque, on teeth, and in oral tissue. Calcium-bound fluoride deposits appear, at least in part, responsible for the cariostatic effect of fluoride and formulations. The compositions and methods of the various embodiments of the present invention enhance the anticaries activity of fluoride therapy. Without wishing to be bound by any theories, it is believed that anticaries activity is enhanced because the compositions and methods increase oral fluoride retention, thereby increasing the concentration of fluoride in saliva and other orals fluids such as plaque fluid.

As used herein, "non-toxic" is intended to conform with accepted and established definitions of safety, such as are described by the designation "generally accepted as safe" by the Food and Drug Administration. Also encompassed in this definition are those compounds that have been added to food for some time and that are recognized as safe under conditions of their intended use. The additives of the various embodiments should be non-toxic enough for oral use at the intended levels on a regular basis and stable for the desired shelf life.

The calcium-containing compounds may be delivered in any suitable form, including but not limited to a mouth rinse, dentifrice, lozenge, confection, chewing gum and similar products, or as additives to these delivery vehicles. As an example, a calcium-containing dentifrice in accordance with the embodiments of the present invention is used before a fluoride rinse. The fluoride also can be contained or encapsulated in the delivery vehicle so that release of calcium and of fluoride occurs sequentially and not concurrently. The release of fluoride from the vehicle preferably occurs after a desired delay. To effect the subsequent administration of fluoride, an amount of fluoride may be encapsulated or contained within a gum, lozenge, candy and the like. For example, a lozenge in which an outer layer contains a soluble calcium compound and an inner layer contains a soluble fluoride compound delivers the calcium and fluoride essentially in sequence as the lozenge dissolves layerwise. In gums as well as lozenges, the fluoride can be encapsulated so that it is released slowly after the more immediate release of calcium.

The embodiments of the present invention can be used with any commercial fluoride product (e.g., rinse) or with products (e.g., lozenges or chewing gum) specifically formulated to take advantage of the chemistry described herein.

Calcium-containing compounds are selected from a number of commercially-available and other compounds that are recognized as food additives in other contexts. Preferred calcium ion-releasing compounds include, but are not limited to, the calcium salts of non-toxic acids having a solubility of at least 0.5 g/L. Examples of such salts are salts of gluconic acid, lactic acid, fumaric acid, glycerophosphoric acid, hydrochloric acid, citric acid, acetic acid, propionic acid, sulfuric acid, and nitric acid and combinations thereof. These calcium salts are believed to be safe at the concentrations described herein. They also are inexpensive and commercially-available.

The concentration of calcium in the delivery vehicle depends at least in part on the form of the selected delivery vehicle. Generally, it is desired to deliver a concentration of soluble calcium in the oral tissue that is effective for reacting with the administered fluoride to form calcium-bound fluoride deposits in plaque, on teeth and in oral tissue In one embodiment of the present invention, the concentration of soluble calcium is at least about 30 mMol per liter (mMol/L) and no more than about 400 mMol/L, preferably at least about 40 mMol/L and less than about 300 mMol/L, more preferably between about 50 mMol/L and about 300 mMol/L, and even more preferably about 150 mMol/L. By way of example, to deliver these concentrations of soluble calcium in the oral cavity, the calcium concentration in a pre-rinse that is used before a fluoride rinse or dentifrice preferably is between about 30 mMol/L to about 400 mMol/L. When formulated as a lozenge, the total calcium content preferably is between about 0.0001 moles to about 0.01 moles. When formulated in a dentifrice, the calcium content preferably is between about 0.002 grams to about 0.5 grams of soluble calcium per gram of dentifrice.

The calcium-containing compound is administered prior to the administration of the fluoride-containing compound. Preferably, there is a delay between administration of the calcium and the fluoride compounds that is short enough to maintain an effective concentration of calcium but long enough to allow the calcium-containing compound to pass from the oral cavity and penetrate into the oral tissue. Preferably, the fluoride-containing compound is administered as soon as practicable after the release of the calcium compound however in some embodiments it may be found desirable to delay the administration of fluoride after a time sufficient to allow at least substantially one exchange of saliva to occur in the oral cavity. In one embodiment, the fluoride-containing compound is administered about one minute, more preferably about two minutes, or more after the administration of the calcium-containing compound.

When the calcium-containing composition is administered prior to a fluoride dentifrice, a reduced concentration of calcium may be possible as a result, at least in part, to the higher concentration of fluoride present in a dentifrice, as compared to a rinse. Therapeutic lozenges or gums also can be formulated to take advantage of the ability of high levels of calcium to increase fluoride deposition. In such products, an outer lozenge layer containing calcium will rapidly release a high level of calcium prior to the subsequent release of fluoride from an interior layer of the lozenge. In gums as well as lozenges, the fluoride can be encapsulated so that it is released slowly after the more immediate release of calcium. It is anticipated that the calcium levels in such products is dependent, at least in part, on the maximum salivary fluoride level induced by the product or method.

In other embodiments, the order of administration may be reversed (i.e. fluoride is administered prior to administration of calcium). Such a reverse system also is expected provide an increase in oral deposition of Ca—F. As with the administration of calcium followed by fluoride, it may be desirable to delay the administration of calcium subsequent to the administration of fluoride.

The anticaries effects of calcium-ion releasing compounds are enhanced further when phosphate in the fluoride component is kept to no more than trace amounts in order to minimize the formation of fluorapatite. For example, the calcium-containing compositions described herein are expected to be compatible with any fluoride rinse or dentifrice having a total phosphate content of less than about 40 parts per million (ppm). A small amount of phosphate may be desirable, however, to prevent, in accordance with published studies (Christoffersen et. al. 1988, *Acta. Odontol. Scand.* 46:325-336), too rapid a formation of Ca—F.

The calcium-containing compositions optionally can include one or more additives to enhance the processability and properties of the compositions. Additives include, but are not limited to, flavorings, colorings, processing aids, pH modifiers, encapsulating components, abrasives, foaming agents, binders, lubricants, fillers and combinations thereof.

EXAMPLES

The following examples further illustrate preferred embodiments of the present invention but are not be construed as in any way limiting the scope of the present invention as set forth in the appended claims.

Preparation of Fluoride and Calcium Rinses

Sodium fluoride solution having a concentration of about 12 mMol per liter (mMol/L) was prepared as a fluoride rinse using conventional methods. This concentration is about the same concentration of fluoride used in commercial over-the-counter fluoride rinses. Calcium lactate solutions were prepared from calcium lactate pentahydrate using conventional methods. Solutions having concentrations of 30 mMol/L, 150 mMol/L, and 300 mMol/L were prepared for use as calcium rinses.

Effects of Calcium Pre-Rinse on Salivary Fluoride Concentration

Five human subjects with normal salivary flow (greater than or equal to about 0.2 mL saliva per minute) rinsed using the solutions described above. Subjects either: (a) rinsed for about one minute with a fluoride rinse or (b) rinsed for one minute with a calcium rinse and then immediately rinsed one minute with a fluoride rinse. Rinsing was conducted at least one hour after eating. Subjects did not follow any special dietary precautions.

Saliva samples were collected from the subjects one hour after rinsing was conducted. The collected saliva was centrifuged. Fluoride in the saliva supernatant was analyzed using a fluoride electrode (see Vogel et al., 1992, *J Dent. Res.* 71:448-52). The results of the saliva analysis are illustrated in FIG. 1.

This example illustrates that calcium pre-rinses increase salivary fluoride concentrations. The increase was statistically significant (p<0.05) when the 150 mMol/L calcium pre-rinse was used. An increase in salivary fluoride concentration also was observed with the 300 mMol/L calcium pre-rinse although the increase was less than the increase observed with the 150 mMol/L calcium pre-rinse. A limited increase in salivary fluoride concentration was found when subjects rinsed with the lowest level of calcium (30 mMol/L) in the pre-rinse.

Effect of Calcium Pre-Rinse on Salivary, Plaque Fluid and Plaque Fluoride Concentrations Thirteen human subjects with normal salivary flow abstained from tooth brushing for two days before rinsing and sample collection. The subjects also fasted before rinsing and sample collection.

Figure 2:
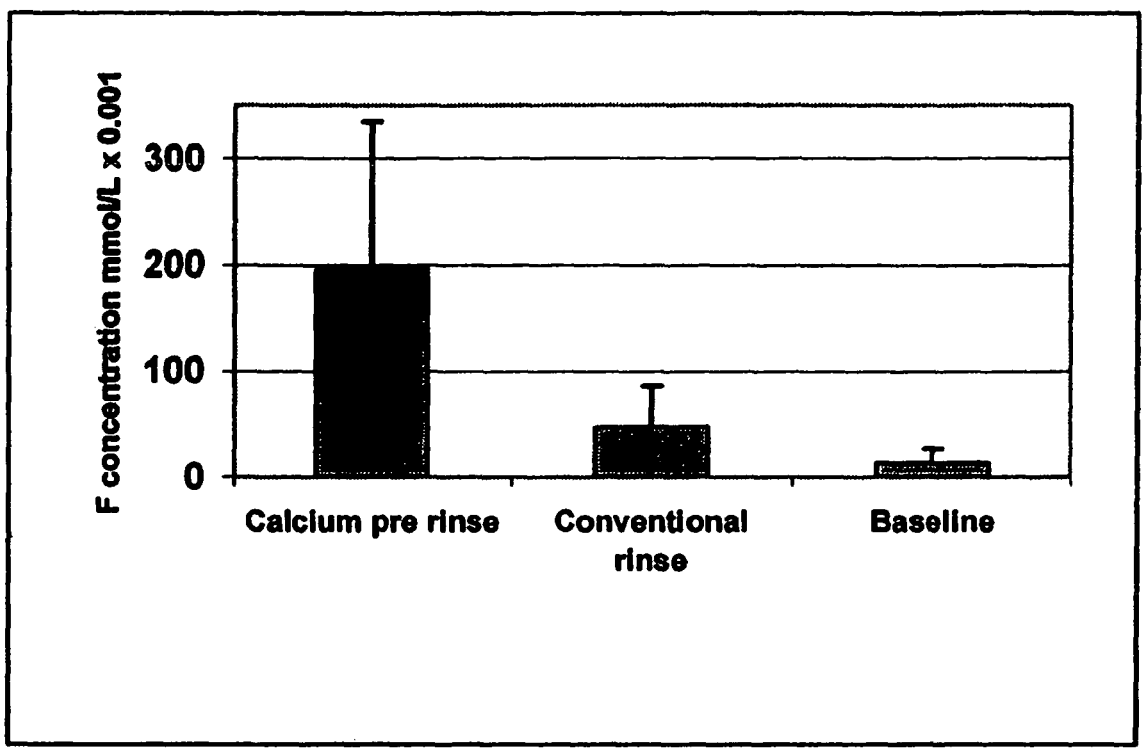
FIG. 2 is a graph showing the recorded concentrations of plaque fluid fluoride from 12 volunteers resulting from use of a conventional fluoride rinse with and without a calcium pre-rinse.
Figure 3:
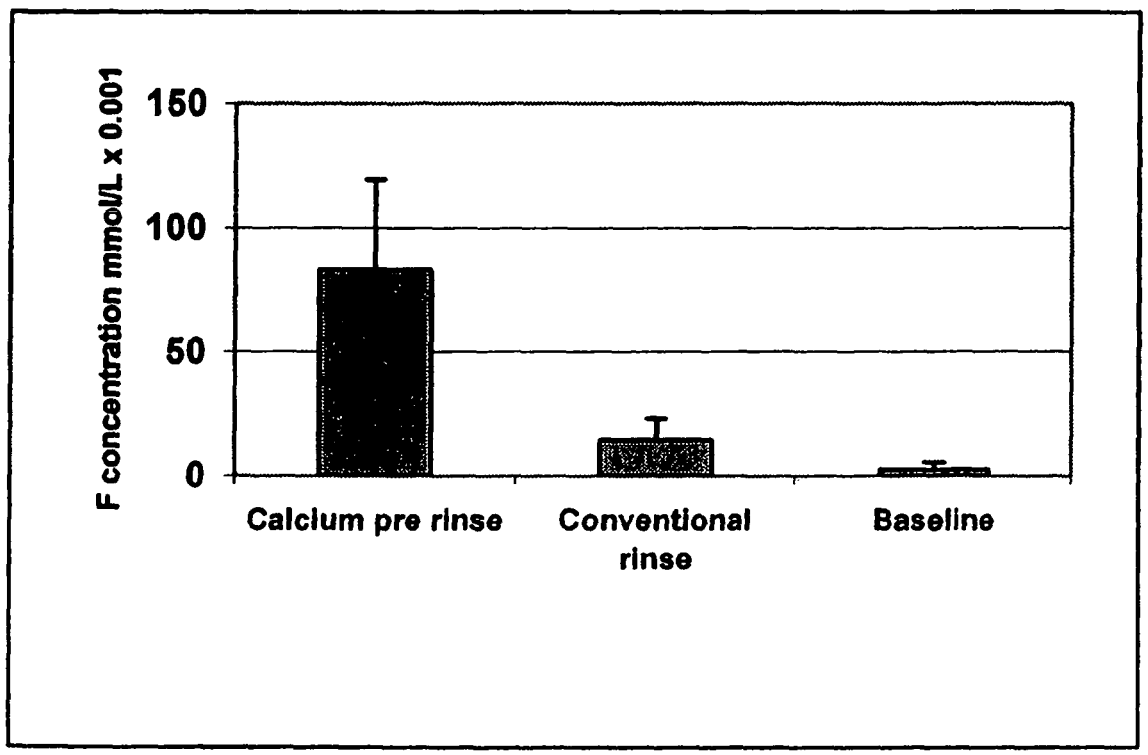
FIG. 3 is a graph showing the recorded concentrations of salivary fluoride from 12 volunteers resulting from use of a conventional fluoride rinse with and without a 150 mmol/L calcium pre-rinse.

The subjects rinsed about one minute with the fluoride rinse described above or rinsed about one minute with a 150 mMol/L calcium solution and then rinsed immediately with the fluoride rinse described above. Plaque and saliva were collected about one hour after rinsing. The collected samples were centrifuged. Fluoride in the saliva supernatant and the fluid phase of plaque was analyzed using a fluoride electrode (see Vogel et al., 1992, *J Dent. Res.* 71:448-52). The results of the saliva and plaque fluid analyses are illustrated in FIGS. 2 and 3, respectively. The results illustrate that using a 150 mMol/L calcium pre-rinse greatly increased plaque fluid and saliva fluoride relative to use of only a conventional fluoride rinse. This increase is statistically significant. The lower salivary fluoride values for the experimental rinse shown in FIG. 3 relative to FIG. 1 are believed to be due to the use of a different and larger subject population in the second experiment (results shown in FIG. 3) who fasted before the experiment, whereas the subjects of the first experiment (results shown in FIG. 1) did not fast.

These results illustrate the discovery that large increases in fluoride in salivary fluid and plaque fluid can be produced when calcium is administered as a pre-rinse before the administration of fluoride. These results also suggest that there is a critical level of calcium required to produce this effect. In these examples, in which fluoride was administered as a rinse with the same fluoride concentration as a commercially available fluoride rinse, a preferred calcium pre-rinse appears to be one with a calcium concentration greater than 30 mMol/L but less than 300 mMol/L.

Although particular embodiments of the present invention have been described and illustrated, it should be understood that the invention is not limited thereto as modifications may be made by persons skilled in the art. The present application contemplates any and all modifications that fall within the spirit and scope of the underlying invention disclosed herein.

What is claimed is:

1. A method of enhancing the cariostatic effect of fluoride on oral tissue, teeth and dental plaque in an oral cavity comprising the steps of:

delivering, in a first delivery vehicle, an amount of a soluble calcium compound into the oral cavity, wherein the first delivery vehicle has a soluble calcium concentration of at least about 30 mMol/L;

allowing calcium ions released from the soluble calcium compound to migrate to and penetrate into the oral tissue, teeth and dental plaque within the oral cavity for a sufficient delay period for solubilized calcium to be cleared from the oral cavity by swallowing or expectoration; and following the delay period, delivering, in a second delivery vehicle, a soluble fluoride-containing compound into the oral cavity whereby said calcium ions react with soluble fluoride ions released from the fluoride-containing compound in the oral cavity to form calcium-bound fluoride deposits on teeth, and in the oral tissue and dental plaque.

2. The method of claim 1, wherein the soluble calcium concentration of the first delivery vehicle is at least about 40 mMol per liter.

3. The method of claim 1, wherein the delay period between delivering the first and second delivery vehicles is about one minute or more.

4. The method of claim 1, wherein the delay period between delivering the first and second delivery vehicles is about two minutes or more.

5. The method of claim 1, wherein the first and second delivery vehicles are in a form selected from the group consisting of a dentifrice, rinse, lozenge confectionary and chewing gum separately or in combination in a manner to deliver the calcium containing compound sequentially before the fluoride containing compound.

6. A method of enhancing the cariostatic effect of fluoride on oral tissue, teeth and dental plaque in an oral cavity comprising:

delivering a pre-rinse that provides a soluble calcium compound into said oral cavity wherein the pre-rinse has a soluble calcium concentration of about 30 to 400 mMol/L;

allowing an amount of calcium ions released from the soluble calcium to migrate and penetrate into the oral tissue, teeth and dental plaque;

following a delay of sufficient time for solubilized calcium to be cleared from the oral cavity by swallowing or expectoration, delivering a fluoride rinse that provides fluoride ions to the oral cavity, whereby said calcium ions released from said soluble calcium compound react with the fluoride ions in the oral tissue, on teeth and in dental plaque to form calcium-bound fluoride deposits in the dental plaque, on teeth and in the oral tissue.

7. The method of claim 1, wherein the second delivery vehicle has a total phosphate content of less than about 40 parts per million (ppm).

8. The method of claim 6, wherein the fluoride rinse has a total phosphate content of less than about 40 parts per million (ppm).

* * * * *

UNITED STATES PATENT AND TRADEMARK OFFICE
CERTIFICATE OF CORRECTION

PATENT NO. : 9,011,823 B2
APPLICATION NO. : 11/048445
DATED : April 21, 2015
INVENTOR(S) : George L. Vogel et al.

Page 1 of 1

It is certified that error appears in the above-identified patent and that said Letters Patent is hereby corrected as shown below:

In the Specification

The following should replace the paragraph at Column 1, Lines 6-10:
STATEMENT OF FEDERALLY SPONSORED RESEARCH
This invention was made with government support under grants DE005354 and DE010840 awarded by the National Institutes of Health. The government has certain rights in the invention.

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*